United States Patent [19]

LeMahieu et al.

[11] Patent Number: 5,620,431
[45] Date of Patent: Apr. 15, 1997

[54] ABSORBENT ARTICLE WITH ELASTICIZED LEG CUFFS

[75] Inventors: Lynn K. LeMahieu, Hortonville; David A. Kuen, Neenah, both of Wis.

[73] Assignee: Kimberly-Clark Corporation, Neenah, Wis.

[21] Appl. No.: 368,057

[22] Filed: Dec. 30, 1994

[51] Int. Cl.$^6$ .................................................. A61F 13/15
[52] U.S. Cl. ................................................ 604/385.2
[58] Field of Search ............................ 604/385.1, 385.2, 604/373

[56] References Cited

U.S. PATENT DOCUMENTS

| | | | |
|---|---|---|---|
| 2,545,674 | 3/1951 | Ralph | 128/287 |
| 3,807,402 | 4/1974 | Miller et al. | 128/287 |
| 3,999,547 | 12/1976 | Hernandez | 128/284 |
| 4,352,355 | 10/1982 | Mesek et al. | 128/287 |
| 4,388,075 | 6/1983 | Mesek et al. | 604/385 |
| 4,573,991 | 3/1986 | Pieniak et al. | 604/385.1 |
| 4,636,207 | 1/1987 | Buell | 604/370 |
| 4,657,539 | 4/1987 | Hasse | 604/385.1 |
| 4,663,220 | 5/1987 | Wisneski et al. | 428/221 |
| 4,675,016 | 6/1987 | Meull et al. | 604/385.2 |
| 4,685,916 | 8/1987 | Enloe | 604/385.1 |
| 4,695,278 | 9/1987 | Lawson | 604/385.1 |
| 4,699,823 | 10/1987 | Kellenberger et al. | 428/219 |
| 4,704,115 | 11/1987 | Buell | 604/385.2 |
| 4,720,415 | 1/1988 | Vander Wielen et al. | 428/152 |
| 4,762,521 | 8/1988 | Roessler et al. | 604/38 |
| 4,795,454 | 1/1989 | Dragoo | 604/385.2 |
| 4,816,025 | 3/1989 | Foreman | 604/385.2 |
| 4,822,435 | 4/1989 | Igaue et al. | 156/164 |
| 4,850,989 | 7/1989 | Villez | 604/385.2 |
| 4,861,652 | 8/1989 | Lippert et al. | 428/284 |
| 4,880,420 | 11/1989 | Pomparelli | 604/385.1 |
| 4,887,602 | 12/1989 | O'Leary | 604/305.1 |
| 4,916,005 | 4/1990 | Lippert et al. | 428/192 |
| 4,925,453 | 5/1990 | Kannankeril | 604/385.1 |
| 4,938,753 | 7/1990 | Van Gompel et al. | 604/385.2 |
| 4,938,754 | 7/1990 | Mesek | 604/385.2 |
| 5,019,067 | 5/1991 | Simmons | 604/385.2 |
| 5,021,051 | 6/1991 | Hiuke | 604/385.2 |
| 5,032,120 | 7/1991 | Freeland et al. | 604/385.2 |
| 5,034,007 | 7/1991 | Igaue et al. | 604/365 |
| 5,087,255 | 2/1992 | Sims | 604/385.1 |
| 5,147,343 | 9/1992 | Kellenberger | 604/368 |
| 5,226,992 | 7/1993 | Morman | 156/62.4 |
| 5,234,422 | 8/1993 | Sneller et al. | 604/385.2 |
| 5,246,432 | 9/1993 | Suzuki et al. | 604/385.2 |
| 5,308,346 | 5/1994 | Sneller et al. | 604/385.2 |
| 5,407,438 | 4/1995 | Hedlund et al. | 604/373 |
| B1 4,315,508 | 11/1988 | Bolick | 604/392 |

FOREIGN PATENT DOCUMENTS

| | | |
|---|---|---|
| 0217032A3 | 4/1987 | European Pat. Off. . |
| 0309246A1 | 3/1989 | European Pat. Off. . |
| 0319314 | 6/1989 | European Pat. Off. . |
| 0374640A2 | 6/1990 | European Pat. Off. . |
| 0376022A2 | 7/1990 | European Pat. Off. . |
| 0409149 | 1/1991 | European Pat. Off. . |
| 0534488 | 3/1993 | European Pat. Off. . |
| 0581258 | 2/1994 | European Pat. Off. . |
| 0604764 | 7/1994 | European Pat. Off. . |
| 0638303 | 2/1995 | European Pat. Off. . |
| 0638302 | 2/1995 | European Pat. Off. . |
| 0681820 | 11/1995 | European Pat. Off. . |
| 2244653 | 12/1991 | United Kingdom . |

OTHER PUBLICATIONS

Method 5514 dated Jul. 20, 1978, "Water Resistance of Cloth"; Low Range, Hydrostatic Pressure Method—Fed. Test Method Std. No. 191A.

*Primary Examiner*—Michael J. Milano
*Attorney, Agent, or Firm*—Thomas M. Gage

[57] ABSTRACT

An absorbent article includes an outer cover, a bodyside liner, and an absorbent assembly disposed between the bodyside liner and outer cover. At least one of the bodyside liner and outer cover form side marginal portions which extend beyond the absorbent assembly. Elastic members of the absorbent article have a width dimension extending between opposite inner and outer edges, an inner zone adjacent the inner edge, and an outer zone adjacent the outer edge. The elastic members are elasticized over substantially the entire width dimension. The outer zone of each of the elastic members is bonded to one of the side marginal portions, and the inner zone of each of the elastic members forms a freestanding leg cuff.

16 Claims, 4 Drawing Sheets

ABSORBENT ARTICLE WITH ELASTICIZED LEG CUFFS

BACKGROUND OF THE INVENTION

The present invention is directed to an absorbent article for containing and absorbing discharged body wastes. More particularly, the invention pertains to a disposable absorbent article having elasticized leg cuffs for enhanced waste containment.

Disposable absorbent articles in fields such as infant care, child care, feminine care and adult incontinency have been constructed in an effort to contain and absorb urine and other body exudates. Most of these absorbent articles have several common components, including a liquid pervious bodyside liner, a liquid impervious backing sheet, an absorbent material disposed between the bodyside liner and the backing sheet, and some form of attachment system for securing the product about the body of the wearer.

In an attempt to improve the containment and absorption abilities of such products, special components have been developed and added to the common components listed above. Leg elastics are one such special component. Leg elastics typically comprise several elastic strands positioned along the sides of the absorbent material and stretch bonded to the liner and backing sheet. The function of the elastic strands is to gather the side portions of the article and form seals or gaskets about the legs of the wearer.

While leg elastics of the foregoing type can provide a demonstrable improvement in waste containment, absorbent articles incorporating such leg elastics may still be subject to failures in the form of leakage around the legs. In part, this may be attributable to the fact that leg elastics are unable to fully conform to the contours of the wearer. Further, existing leg elastics are believed to be a potential source of discomfort to the wearer. It is hypothesized that the gatherable materials to which the elastic strands are attached tend to form multiple pleats along the length of the strands when the elastic strands are in a semi-relaxed state. During movements, the pleats may rub against the wearer, leading to irritation or chafing. Because increased tension may simply increase the formation of pleats and exacerbate skin irritation, increasing the tension of conventional leg elastics to improve conformity about the wearer is not presently a viable alternative.

Therefore, what is lacking and needed in the art is an improved absorbent article that provides enhanced containment of wastes while maintaining the comfort of the wearer.

SUMMARY OF THE INVENTION

In response to the discussed deficiencies in the prior art, a new disposable absorbent article has been developed. The absorbent article functions to contain and absorb discharged body wastes while also being comfortable to wear.

One aspect of the invention pertains to an absorbent article including an outer cover having longitudinal end edges and longitudinal side edges extending between the end edges. The absorbent article also includes a bodyside liner bonded to the outer cover and an absorbent assembly disposed between the bodyside liner and outer cover. At least one of the bodyside liner and outer cover form side marginal portions which extend beyond the absorbent assembly. Elastic members of the absorbent article have opposite end edges, opposite inner and outer edges extending between the end edges and defining a width dimension, an inner zone adjacent the inner edge, and an outer zone adjacent the outer edge. The outer zone of each of the elastic members is bonded to one of the side marginal portions, and the inner zone of each of the elastic members forms a freestanding leg cuff. The elastic members are elasticized over substantially the entire width dimension and the absorbent article has a leg cuff tension of at least about 0.2 kilogram.

This aspect of the invention provides an absorbent article with outer leg cuffs and inner freestanding leg cuffs. A substantial amount of elastic material is in contact with the wearer to conform to the topography of the wearer and form seals about the legs of the wearer. Tension of the elastic members is dissipated over a relatively large area to provide a particularly comfortable and nonirritating fit. Further, these relatively high degrees of tension are obtained without high degrees of elongation of the elastic members.

In other aspects of the invention, at least a portion of the outer zone of each of the elastic members extends transversely outward from side edges of the outer cover, and the elastic members comprise a breathable material having an air porosity value of at least about 150 cubic feet per minute per square foot in a relaxed state. This aspect of the invention provides a path of air permeability through the absorbent article to allow adequate air flow adjacent the body of the wearer. Further in this regard, the elastic members may be formed of a substantially liquid-impermeable material or treated to be substantially liquid impermeable in order to resist leakage.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Figure 1:
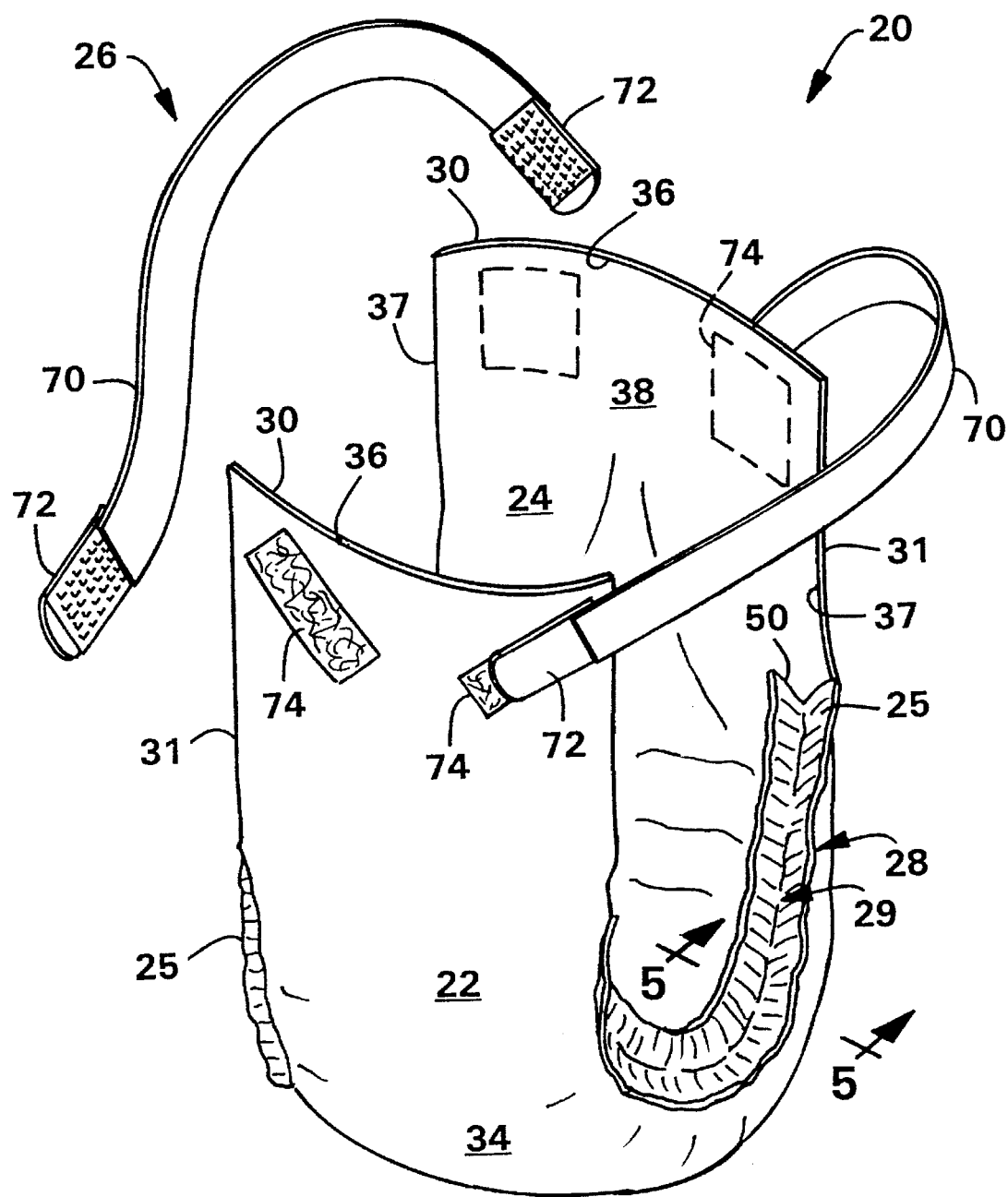
FIG. 1 is a perspective view of a disposable absorbent article according to the present invention.

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use, and not intended to be washed and reused.

(c) "disposed," "disposed on," "disposed with," "disposed at," "disposed near," and variations thereof are intended to mean that one element can be integral with another element, or that one element can be a separate structure bonded to or placed with or placed near another element.

(d) "elastic," "elasticized" and "elasticity" mean that property of a material by virtue of which it tends to recover its original size and shape after removal of a force causing a deformation.

(e) "elongation" means the ratio of the extension of a material to the length of a material prior to stretching, expressed in percent.

(f) "extension," "extend" and "extended" mean the change in length of a material due to stretching, expressed in units of length.

(g) "force" includes a physical influence exerted by one body on another which produces acceleration of bodies that are free to move and deformation of bodies that are not free to move. Force is expressed in grams per unit area.

(h) "freestanding" refers to a particular portion of a first element, which portion is not bonded to a second element and is capable of moving relative to the second element.

(i) "integral" is used to refer to various portions of a single unitary element rather than separate structures bonded to or placed with or placed near one another.

(j) "liquid impermeable" when used to describe a layer or laminate means that liquid such as urine will not pass through the layer or laminate under ordinary use conditions in a direction generally perpendicular to the plane of the layer or laminate at the point of liquid contact.

(k) "member" when used in the singular can have the dual meaning of a single element or a plurality of elements.

(l) "operatively joined", with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(m) "outward" refers to a position relative to the center of an absorbent garment, and particularly transversely and/or longitudinally away from the longitudinal and transverse center of the absorbent garment.

(n) "stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

(o) "stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

These terms may be defined with additional language in the remaining portion of the specification.

DETAILED DESCRIPTION OF THE PREFERRED EMBODIMENTS

With reference to FIGS. 1–4, a disposable absorbent article formed according to the invention is shown for purposes of illustration as an adult incontinence garment 20. The invention may also be embodied in other types of absorbent articles such as diapers, diaper pants, feminine napkins, children's training pants, or the like.

The incontinence garment 20 generally includes an outer cover 22, an absorbent assembly 23, a bodyside liner 24, and elastic members 25. These components are maintained in position about the wearer with an attachment system 26 (FIG. 1). The elastic members 25 are disposed at the longitudinal sides of the garment 20 and form both outer leg cuffs 28 and inner freestanding leg cuffs 29. The elastic members 25 provide relatively high levels of tension so that the absorbent article 20 tends to maintain a close fit to the body of the wearer. Due to the nature of the elastic members 25 employed and their integration with the other components of the garment 20, the garment readily conforms to the wearer while minimizing the occurrences of skin marking. As a result, the garment 20 provides enhanced containment of wastes while maintaining the comfort of the wearer. The components of the incontinence garment 20 and their method of assembly will now be described in more detail.

Figure 2:
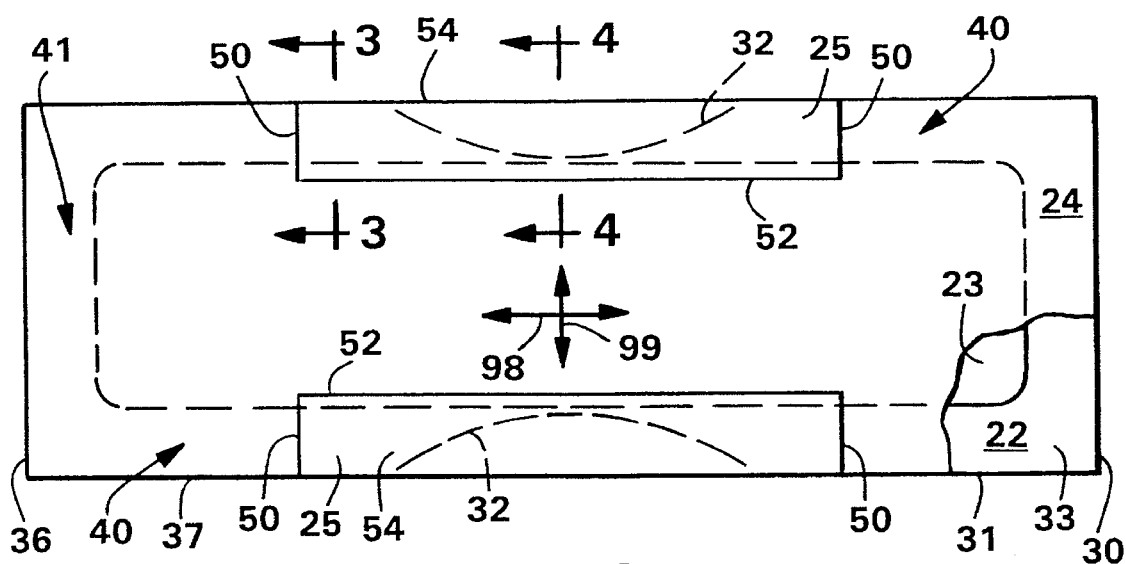
FIG. 2 is a top plan view of several components of the disposable absorbent article shown in FIG. 1, in a flat and stretched condition and with portions broken away for purposes of illustration.

For purposes of identifying positional relationships of various components, the shape of the garment 20 will be considered to define a longitudinal axis, represented by arrow 98, and a transverse axis, represented by arrow 99 (FIG. 2). The longitudinal axis 98 intersects the ends of the garment, and the transverse axis 99 is generally perpendicular to the longitudinal axis and located midway between the ends.

The outer cover 22 has opposite longitudinal end edges 30 (FIG. 1) and opposite longitudinal side edges 31 (FIGS. 1–4) that extend between the end edges. Desirably, the outer cover 22 is generally I-shaped or hourglass-shaped whereby each side edge 31 of the outer cover defines a recessed portion 32 (FIGS. 2 and 4) approximately midway between the end edges 30. The recessed portions 32 may also be skewed toward one end edge 30 of the outer cover (not shown). The recessed portions 32 may constitute, for example, from about 15 to about 75 percent of the longitudinal length dimension of the outer cover. Alternatively, the outer cover 22 can be rectangular, T-shaped or irregularly-shaped. The outer cover 22 also has opposite major surfaces, designated interior surface 33 and garment-facing surface 34.

The outer cover 22 desirably comprises a material that is formed or treated to be liquid impermeable. Alternatively, the outer cover 22 may comprise a liquid permeable material and other suitable means (not shown), such as a liquid impermeable layer associated with the absorbent assembly 23, may be provided to impede liquid movement away from the absorbent assembly. The outer cover 22 may also be gas permeable, such that gases encountered during use of the absorbent garment are able to pass through the material under ordinary use conditions, over either all or part of its surface area.

The outer cover 22 may comprise a single layer of material or a laminate of two or more separate layers of material. Suitable outer cover materials include films, wovens, nonwovens, laminates of films, wovens, and/or nonwovens, or the like. For example, the outer cover 22 may comprise a thin, substantially liquid impermeable web or sheet of plastic film such as polyethylene, polypropylene, polyvinyl chloride or similar material. The outer cover material may be transparent or opaque and have an embossed or matte surface. One particular material for the outer cover 22 is a polyethylene film that has a nominal thickness of about 0.025 millimeter and a systematic matte embossed pattern, and that has been corona treated on both sides. Another suitable outer cover material is an adhesive or thermal laminate comprising a cast or blown film formed of polypropylene, polyethylene or the like, and a spunbond web formed of polypropylene fibers or polypropylene and polyethylene medium-crimped bicomponent fibers in a 50/50 side-by-side configuration.

The absorbent assembly 23, which is disposed on the interior surface 33 of the outer cover 22, comprises materials adapted to absorb and retain liquid waste. The absorbent assembly 23 may be rectangular as illustrated, or T-shaped, I-shaped or irregularly-shaped, and is narrower and desirably also shorter than the outer cover 22. The absorbent assembly 23 may be bonded to the outer cover 22 using adhesives, ultrasonic bonds, thermal bonds, or other suitable means.

The absorbent assembly 23 may comprise various absorbent materials, such as an air-formed batt of cellulosic fibers (i.e., wood pulp fluff) or a coform material composed of a mixture of cellulosic fibers and synthetic polymer fibers. The absorbent assembly 23 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 1987, to Kellenberger et al. and U.S. Pat. No. 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent assembly 23 may also include tissue layers or acquisition or distribution layers to help maintain the integrity of fibrous absorbents or transport liquids (not shown).

The bodyside liner 24 has opposite longitudinal end edges 36 (FIGS. 1 and 2) and opposite longitudinal side edges 37 (FIGS. 1–4) that extend between the end edges. The bodyside liner 24 may be generally rectangular as illustrated, or alternatively I-shaped, T-shaped or irregularly-shaped. The bodyside liner 24 has opposite major surfaces, designated bodyside surface 38 and interior surface 39. The bodyside liner 24 is desirably coextensive with the outer cover 22, except in the area of the recessed portions 32 where the bodyside liner 24 may extend transversely outward beyond the side edges 31 of the outer cover.

Figure 3:
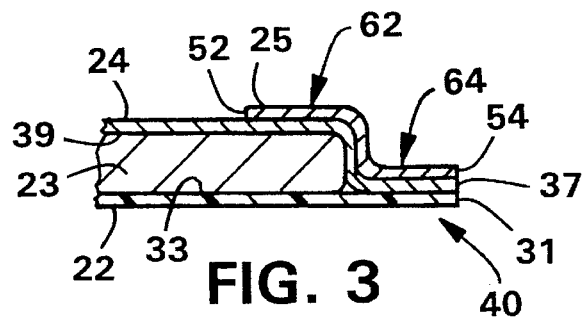
FIG. 3 is an enlarged section view taken generally from the plane of the line 3—3 in FIG. 2.
Figure 4:
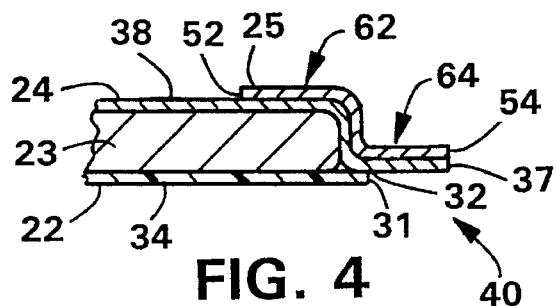
FIG. 4 is an enlarged section view taken generally from the plane of the line 4—4 in FIG. 2.

With particular reference to FIGS. 2–4, the outer cover 22 and bodyside liner 24 desirably extend transversely and longitudinally beyond absorbent assembly 23 to form side marginal portions 40 and end marginal portions 41, respectively. The absorbent assembly 23 is disposed between the interior surface 33 of the outer cover 22 and the interior surface 39 of the bodyside liner 24, and the outer cover and bodyside liner are desirably bonded together in these marginal portions 40 and 41 using adhesives, thermal bonds, ultrasonic bonds or other suitable means. The bodyside liner 24 may also be bonded directly to the absorbent assembly 23.

The bodyside liner 24 is formed of a liquid permeable material so that liquid waste, and possibly semi-solid waste as well, can pass through the liner and be absorbed by the absorbent assembly 23. Suitable bodyside liners 24 may comprise a nonwoven web or sheet of wet strength tissue paper, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 24 is desirably non-elastic and may be treated with a surfactant to aid in liquid transfer.

As illustrated, the elastic members 25 are separate elements bonded to the bodyside surface 38 of the bodyside liner 24. The elastic members 25 are shown in a relaxed condition in FIGS. 1 and 5 and in a flat and stretched condition in FIGS. 2–4. Each of the elastic members 25 has opposite longitudinal end edges 50 and opposite inner and outer edges 52 and 54 which extend between the end edges.

The distance between the end edges 50 of an elastic member 25 defines a length dimension. The elastic members 25 are elasticized in the direction of their length dimension. The length dimension is measured while the elastic member 25 is in a generally stretched condition, so that the material to which it is attached, in this case the bodyside liner 24, is generally ungathered. The length dimension is desirably greater than the longitudinal extent of the recessed portions 32 and less than the full length of the garment 20. In particular embodiments, the length dimension represents from about 30 to about 70 percent of the length of the garment 20, for example from about 20 to about 50 centimeters, and more desirably from about 30 to about 40 centimeters.

The distance between the inner and outer edges 52 and 54 of an elastic member 25 defines a width dimension, which can be measured with the elastic member in a relaxed condition. The width dimension is desirably greater than the transverse depth of the recessed portions 32. In particular embodiments, the width dimension is from about 15 to about 70 millimeters, and more desirably from about 20 to about 60 millimeters for improved performance.

The elastic members 25 desirably comprise materials that enable the elastic members to be elasticized over substantially the entire width dimension. With additional reference to FIG. 5, each elastic member 25 can be viewed as an integral element comprising an inner zone 62 adjacent the inner edge 52 and an outer zone 64 adjacent the outer edge 54 and abutting the inner zone 62. The elastic members 25 are desirably elasticized in the direction of their length dimension in both of the inner and outer zones 62 and 64.

The elasticity of an elastic member 25 over its width dimension can be characterized by one panel, three panel, and eight panel tension values. The elastic members 25 desirably have a one panel tension value of at least about 800 grams, and more desirably at least about 1080 grams. In particular embodiments, the elastic members 25 have a three panel tension value of at least about 100 grams, and more desirably a three panel tension value of at least about 170 grams, such as 187 grams. Moreover, the elastic members 25 in particular embodiments have an eight panel tension value of at least about 15 grams, and more desirably a eight panel tension value of at least about 25 grams, such as 58 grams.

The following "Material Tension Test" is a suitable technique for determining the one, three and eight panel tension values of the elastic material used to fabricate the elastic members 25. In general, the test determines the stress/strain curve and measures the tension of elastic fabrics at the stress-strain inflection point. The Material Tension Test employs the equipment listed below.

1. A rectangular template measuring 7.62 cm by 17.78 cm.
2. A Constant Rate of Extension (CRE) type tensile testing machine capable of being controlled by testing software. One suitable device is a Sintech System 2 tensile tester available from Sintech, Inc., of Research Triangle Park, N.C., U.S.A.
3. Control software for the tensile testing machine. One company versed in such software is Sintech, Inc.
4. Pneumatic action grips identified as Series 2712, 200 pound capacity, available from Instron Corporation, of Canton, Mass., U.S.A.
5. Rubber-coated grip faces measuring 2.54 cm by 7.62 cm, which are inserted into the pneumatic action grips to hold the test material in the tensile testing machine. Suitable grip faces are available from Instron Corporation.
6. A 10 pound load cell available from Sintech, Inc. or a 50 kilogram load cell available from Instron Corporation.
7. A printer which is compatible with the control software.
8. Scissors
9. Marker The equipment is set up according to the following procedure.

1. Insert the rubber coated grip faces into the pneumatic action grips and install the pneumatic action grips on the tensile testing machine.
2. Verify that the appropriate load cell is in the tensile tester and allow the load cell to warm up for a minimum of 30 minutes.
3. Boot up the control software, and then follow the menu selection to designate the following parameters:
    1. Crosshead Speed 500 mm/MIN
    2. Full Scale Load 4540 Grams
    3. Gage Length 50 mm
    4. Stop Load 2000 Grams
    5. Segment Length 10%
    6. Slope Tolerance 5%

Note that the Full Scale Load setting may vary depending on the load cell.
4. Calibrate the load cell. Note that the load cell is to be calibrated whenever the load cell or a data disk is changed.
5. Set the gage length to 50 mm.

The elastic material to be tested is conditioned in a standard-condition atmosphere of 23°±1° C. (73.4°±1.8° F.) temperature and 50±2% relative humidity for 4 hours. The material to be tested is placed on a flat surface and the direction of elasticity is noted. Using the template, marker and scissors, a rectangular specimen measuring 7.62 cm by 17.78 cm is cut so that the long dimension of the specimen is parallel to the direction of elasticity. All the edges of the specimen must be clean cut and straight. The specimen can then be tested by the following procedure.

1. Insert a test specimen between the grips so that it is hanging vertically without twisting. Note that the specimen must be inserted such that the load cell registers a pre-load of more than 2 grams and less than 10 grams.
2. Start the crosshead in motion so that it elongates the test specimen to the 2000 gram stop load.
3. Observe the graphics display during the test. Abnormalities caused by slippage or incorrect clamping may be apparent in the curve or slope line which could result in a negative or zero slope. Discard negative or zero slope results and sample. Adhesive on the grip faces can create a slippage problem. Note and record slippage or any other abnormalities.
4. When the test is complete, remove the specimen. Determine the tension of the specimen in grams at the stress-strain inflection point. This tension value is the one panel tension value.
5. To determine a three panel tension value for a material, the procedure for determining the one panel tension value is modified as follows. One 3.175 by 17.78 centimeter rectangular test specimen, which is smaller than the specimen used in the one panel procedure, is cut into three strips designated A, B and C of equal width, which is approximately 10.58 millimeters. One of the three strips is placed between the grips of the tensile tester. The tension in grams at the stress-strain inflection point is recorded. The stop load is incrementally changed from 2000 grams to 333 grams to account for the change in specimen size and sample distortion such as neckdown. The test is repeated for the other two strips from the test specimen. The lowest tension value among strips A, B and C is recorded as the three panel tension value.

To determine an eight panel tension value for a material, the procedure for determining the one panel tension value is modified as follows. One 3.175 by 17.78 centimeter rectangular test specimen is cut into eight strips designated A, B, C, D, E, F, G and H of equal width, which is approximately 3.97 millimeters. One of the eight strips is placed between the grips of the tensile tester. The tension in grams at the stress-strain inflection point is recorded. The stop load is incrementally changed from 2000 grams to 125 grams to account for the change in specimen size and sample distortion such as neckdown. The test is repeated for the other seven strips from the test specimen. The lowest tension value among strips A, B, C, D, E, F, G and H is recorded as the eight panel tension value.

In one particular embodiment, the elastic members 25 comprise an elastic, cloth-like, nonwoven fibrous material, such as an elastic stretch bonded laminate web or an elastic meltblown web. Examples of suitable elastic meltblown fibrous webs for forming elastic members 25 are described in U.S. Pat. No. 4,663,220 issued May 5, 1987, to T. Wisneski et al., which is incorporated herein by reference. Examples of suitable composite fabrics comprising at least one layer of nonwoven textile fabric secured to a fibrous elastic layer are described in European Patent Application EP 0 110 010 published on Apr. 8, 1987, with the inventors listed as J. Taylor et al. which is incorporated herein by reference.

In yet another aspect of the invention, the elastic members 25 can comprise an elastic, stretchable composite web comprising a suitable number of individual, discrete strips of elastic material secured to one or more nonwoven fibrous layers. Such a composite web may, for example, comprise a selected pattern of individual elastic strips operably secured to a nonwoven fibrous layer or between two nonwoven layers. The elastic strips may, for example, be composed of a thermoplastic, melt extrudable material. Examples of suitable elastic materials include polyether-polyamide block copolymers, polyurethanes, synthetic linear A-B-A and A-B block copolymers, chlorinated rubber/EVA (ethylene-vinyl acetate) blends, EPDM (ethylenepropylene diene monomer) rubbers, EPM (ethylene-propylene monomer) rubbers, blends of EPDM/EPM/EVA, and the like. Examples of such composite webs are disclosed in U.S. patent application Ser. No. 316,185 filed Sep. 30, 1994, by Yeo et al. and titled "Perimeter Barrier For Personal Care Absorbent Articles And The Like" (Attorney Docket No. 11,501), which is incorporated herein by reference.

Alternatively, the elastic members 25 may comprise a neck bonded laminate material, an elastic film, an elastomeric foam material, or the like. Examples of neck bonded laminate materials are described in U.S. Pat. No. 5,226,992 issued Jul. 13, 1993, to Morman, the disclosure of which is incorporated herein by reference. The elastic members 25 may also comprise combinations of several elastic materials.

In one aspect of the invention, the elastic members 25 comprise an elastic web which is substantially air-permeable so as to provide breathability to the outer leg cuffs 28 and inner freestanding leg cuffs 29. The elastic members 25 may have an air porosity value of at least about 150 cubic feet per minute per square foot (cfm/ft$^2$) in the relaxed state, and at least about 200 cfm/ft$^2$ at the maximum nondestructive elongation (stretch to stop). In particular embodiments, the elastic members 25 have an air porosity value of at least about 250 cfm/ft$^2$ in a relaxed state.

A suitable technique for determining the air porosity value is the following "Porosity Test," which employs a Frazier Air-Permeability Tester, manufactured by Frazier Precision Instrument Co. of Silver Springs, Md., U.S.A., or its equivalent. For the purposes of the present Porosity Test, the Frazier instrument is configured with its 11 millimeter (mm) or 16 mm diameter top attachment orifice, and an appropriate air orifice in the air tank. A sample is cut from the material used to form the elastic members 25. The test sample measures 12.7 by 12.7 cm and can be placed over the attachment orifice in either its relaxed state or its elongated state. The orifice should be completely and securely covered with no gaps and no wrinkles in the sample. The test sample is then clamped in position employing the clamping device on the Frazier apparatus. The Frazier instrument has a Powerstat control, an inclined manometer and a vertical manometer. The Powerstat is adjusted until the oil column in the inclined manometer reaches the 0.5 value. At this point, the pressure drop indicated by the vertical manometer should read at least 3 inches. If this pressure drop is less than 3 inches, the Frazier instrument should be configured with a smaller flow nozzle orifice in order to provide the desired 3 inch pressure drop, if possible. The procedure for changing the appropriate nozzle is described in the instructions supplied with the Frazier instrument. After the inclined manometer oil column has steadied at the proper level, the level of the oil in the vertical manometer is read and recorded. The vertical manometer reading is then converted to a flow rate in units of cubic feet of air per minute per square foot of sample by employing the calibration/conversion table supplied with the Frazier instrument. It should be noted that the Frazier instrument has a lower measurement limit of 3 cfm/ft$^2$.

In another aspect of the invention, the elastic members 25 are composed of an elastic web which is substantially liquid-impermeable. Desirably, the elastic members 25 have a resistance to water penetration of at least about 30 centimeters, and more particularly at least about 90 centimeters, as determined using Method 5514 of Federal-Test Methods Standard No. 191A, which is incorporated herein by reference.

Figure 6:
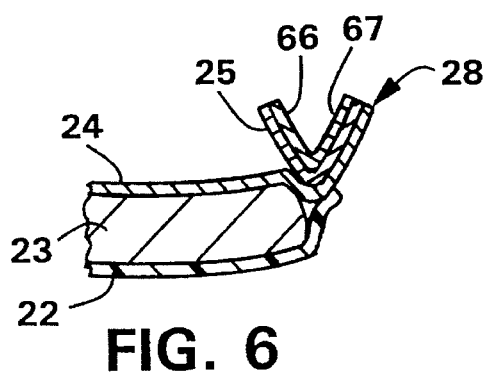
FIG. 6 is a section view similar to FIG. 5, but illustrating components of an alternative disposable absorbent article according to the present invention.

The elastic members 25 may comprise a substantially liquid-impermeable material or be treated to be substantially liquid impermeable. For example, an alternate construction of an elastic member 25 is illustrated in FIG. 6. The elastic member 25 comprises a stretch bonded laminate of an elastic layer 66 and a liquid impermeable layer 67. The liquid impermeable layer 67 may comprise a polyethylene film or the like.

The elastic members 25 may be operatively joined to the side marginal portions 40 using adhesives, ultrasonic bonds, thermal bonds, or other suitable means. The elastic members 25 may be stretch bonded to the side marginal portions 40 or bonded in a relaxed state to a gathered portion of the side marginal portions. As one illustration of stretch bonding, each elastic member 25 may be stretched to at least about 1.6 times its relaxed length and bonded to the bodyside surface 38 of the bodyside liner 24 using a hot melt adhesive. The adhesive may comprise a hot melt adhesive applied by various techniques, such as spraying, slot-coating extrusion, printing or the like. Suitable adhesives are available from Findley Adhesives, Inc., Wauwatosa, Wis. Application of the elastic members 25 may alternatively be accomplished by other methods known in the art.

As illustrated best in FIGS. 2–4, the elastic members 25 are desirably positioned in the side marginal portions 40 so that the elastic members span the recessed portions 32 of the outer cover 22. In this way, the elastic members 25 can be bonded to the side marginal portions 40 longitudinally between the recessed portions 32 and the end edges 36 of the bodyside liner 24. Specifically in regard to the transverse direction, the elastic members 25 are desirably positioned so that at least a portion of the outer zone 64 of each elastic member 25 is located transversely outward from the side edge 31 of the outer cover 22. With particular reference to FIG. 4, at least a portion of the outer zone 64 of the elastic member 25 is located transversely outward from the side edge 31 of the outer cover, at least over the extent of the recessed portions 32.

Figure 5:
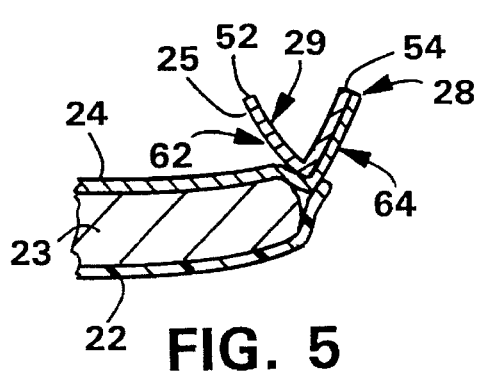
FIG. 5 is a section view taken generally from the plane of the line 5—5 in FIG. 1.

The inner zones 62 of the elastic members 25 are desirably not bonded to the side marginal portions 40. When the elastic members 25 are allowed to contract as illustrated in FIGS. 1 and 5, the inner zones 62 tend to stand up from the bodyside liner 24 and form the inner freestanding leg cuffs 29. The inner zone 62, defined as that portion of the elastic member 25 that is contiguous with the inner edge 52 and not bonded to the bodyside liner 24, desirably has a width dimension measured between the inner edge 52 and the abutting outer zone 64 of at least about 4 millimeters, such as from about 4 to about 50 millimeters, and more particularly from about 8 to about 38 millimeters for improved performance. Correspondingly, the outer zone 64 is defined as that portion of the elastic member 25 between the inner zone 62 and the outer edge 54. The outer zone 64 suitably has a width dimension measured between the inner zone 62 and the outer edge 54 of at least about 6 millimeters, and desirably from about 8 to about 50 millimeters.

The incontinence garment 20 is held in place about the wearer with the attachment system 26. The illustrated attachment system 26 includes a pair of elastic straps 70, hook members 72 at each end of each strap, and loop members 74 bonded to the outer cover 22 for releasably engaging the hook members. As an alternative to hook-and-loop fasteners, the elastic straps 70 could be attached to the outer cover 22 using other types of fasteners (not shown), such as buttons, buckles, snaps or the like. Still alternatively, the garment 20 could be maintained about the body of the wearer with other attachment systems (not shown), such as tapes, a belt, cohesive strips or the like. Suitable attachment systems are disclosed in U.S. Pat. No. 4,315,508 issued Nov. 8, 1988, to Bolick, which is incorporated herein by reference.

In use, the incontinence garment 20 is positioned about the wearer to receive solid and liquid waste and secured with the attachment system 26. The outer leg cuffs 28 tend to form seals about the legs of the wearer to minimize leakage. The inner freestanding leg cuffs 29 are raised from the top surface of the bodyside liner 24 and act as a first impediment to lateral movement of body wastes toward the outer leg cuffs 28, thus assisting in containment.

Due to the nature of the elastic members 25 and their incorporation in the garment 20, a substantial amount of elastic material in terms of surface area is in contact with the wearer. It is hypothesized that the outer leg cuffs 28 in particular are especially suited to forming seals about the legs as the wide elastic is able to conform over two-dimensions to the anatomical topography. The tension of the elastic members 25 is also dissipated over a greater area making the fit particularly comfortable and nonirritating. The selected elastic members 25 advantageously tend to form smaller, more uniform pleats which are less abrasive than those formed by conventional strand elastic leg gathers having only a relatively small number of strands.

The incontinence garment 20 illustrated in FIGS. 1–5 is particularly adapted to allow air flow adjacent the body of the wearer. Specifically, where the elastic members 25 are formed of breathable materials and positioned to span the recessed portions 32, a path of air permeability is established. The elastic members 25 may be formed of a substantially liquid-impermeable material or treated to be substantially liquid impermeable to resist leakage. Further, it is hypothesized that the elastic members 25 spanning the recessed portions 32 add to the comfort of the wearer.

In one aspect of the invention, the garment 20 can provide relatively high degrees of tension without creating localized regions of high tension that contribute to skin irritation. Also, the relatively high degrees of tension can be obtained with relatively low elongation of the elastic members 25. In particular, the leg cuff region of the garment 20 desirably possesses a leg cuff tension of at least about 0.2 kilogram, and more desirably at least about 0.25 kilogram. With the elastic members 25 bonded to the side marginal portions 40 at less than about 75 percent elongation, the leg cuff region of the garment 20 desirably possesses a leg cuff tension of at least about 0.20 kilogram.

Figure 7:
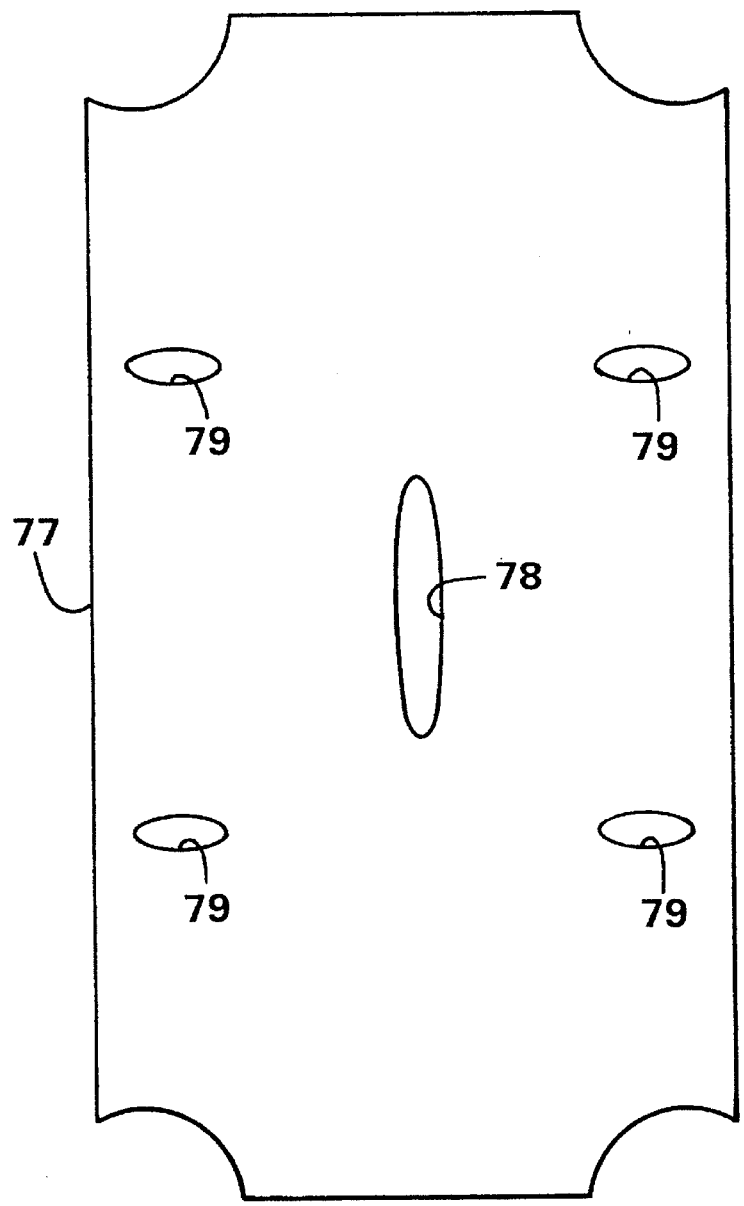
FIG. 7 is a top plan view of a template used in a Product Tensile Test.

A suitable technique for determining the elasticized leg cuff tension value is the following "Product Tension Test," which determines the tension of the leg cuff region of the garment 20 at a predetermined amount of stretch. The leg cuff regions of the garment 20 include portions of the side marginal portions 40 and include the elastic members 25. The Product Tension Test uses the following equipment and materials:

1. A lightbox mounted in a vertical position with clamps along the top edge.
2. A double clamp weight weighing 1000±5 grams.
3. A template 77 with a centerline reference 78, as illustrated in FIG. 7. The template has a length of 64.4 cm. Along each side of the template, a pair of apertures 79 are centered along the length of the template. The apertures in each pair are separated so that pen marks on a product made through the apertures are separated by 25.4 cm. This distance may need to be modified, for example to 17.78 cm when smaller products such as diapers or training pants are tested. The apertures are spaced from the centerline reference a sufficient distance so that the marks correspond to the lateral location of the elastic members 25.
4. An elastic tension tester such as a Chatilion DFG2 force gauge available from John Chatilion & Sons Inc. located in New York, N. Y., U.S.A. The force gauge has upper and lower clamps, such as 3 inch Bulldog clamps.
5. An aluminum gage rod measuring 20.3 cm (8 inches) long. The length may be adjusted to 16 cm for smaller products as noted above.
6. Pen with black ink.
7. Weights for calibration, 50, 100, 200, 500 grams, traceable to the National Bureau of Standards (NBS).
8. Scissors
9. Ruler A garment 20 should be tested no sooner than 4 hours after it is produced. The garment 20 to be tested is conditioned in a standard-condition atmosphere of 23°±1° C. (73.4°±1.8° F.) temperature and 50±2% relative humidity for 4 hours. The equipment is set up in the following manner:

1. Turn on the Chatilion force gauge and allow 10 minutes for the unit to warm-up.
2. Calibrate the Chatilion force gauge using the calibration weights according to the manufacturer's instructions.
3. While supporting the force gage assembly, loosen the locking knob on the back of the force gage assembly. Position the force gage assembly to give approximately 20.3 cm (16 cm for smaller products) of space between the upper and lower clamps. Retighten the locking knob to hold the force gage assembly in place.
4. Hold the gage rod between the upper and lower clamps. Use the fine adjustment knob located above the force gage to adjust the distance until both clamps just touch the rod.
5. Verify that the units of measure on the force gage is set to kilograms. If required, push the "zero" button to zero the display.

The test specimens are prepared in the following manner. The garment 20 is centered beneath the lightbox clamps and hung with the outer cover 22 against the lightbox. If possible, the clamps are attached to avoid the absorbent assembly 23 of the garment 22. The double clamp weight is attached to the lower end of the garment and gently lowered. Next, the template is centered on the garment 20 and each elastic member 25 is marked with the pen through the apertures. The procedure is repeated until a total of 5 garments are marked. Each garment has two leg cuff regions so there are a total of 10 test specimens.

Each of the 10 test specimens can then be tested by the following procedure.

1. Cut the leg cuff regions from each garment while it is hanging. Use the scissors to make a crosswise cut to the absorbent batt about ½ inch (13 mm) beyond the black ink mark. Cut lengthwise between the elastic and the absorbent batt extending to ½ inch (13 mm) beyond the black ink mark on the other end of the elastic member. Then make a crosswise cut to free the elastic member from the garment. If the absorbent batt must be cut to remove the elastic members, the absorbent batt should be cut to remove as much absorbent material from the test specimen as possible.
2. Wait 30 minutes but no more than 60 minutes from the time of cutting before testing the specimen.
3. Place one end of the specimen into the upper clamp so the black line coincides with the leading edge of the clamp. Take care so a foldover in the liner does not get trapped in the clamp, as this may give erroneously high results.
4. Press the "ZERO" button to tare the weight of the specimen.
5. Unhook the lower slider, raise it up, and place the bottom of the specimen in the lower clamp so the marked line coincides with the leading edge of the clamp. The small reading showing on the display should have no effect on the final value.
6. Gently, lower the "Sample" sleeve over a three second time interval until it touches and latches to the bottom latch.
7. Wait 5 seconds, then check the alignment of the black lines with the clamps. If no slippage has occurred, record the reading on the force gauge. If slippage has occurred, replace the clamps as needed and test a new specimen.

The leg cuff tension is the average of the 10 measured values.

Figure 8:
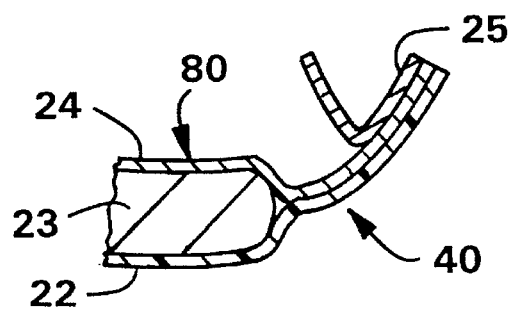
FIG. 8 is a section view similar to FIG. 5, but illustrating components of another alternative disposable absorbent article according to the present invention.

An alternative incontinence garment 80 according to the present invention is partially shown in FIG. 8, where components similar to those previously described have been given the same reference numeral. The outer cover 22 and bodyside liner 24 of the garment 80 are coextensive about their entire peripheries. As a result, no recessed portions are formed similar to the recessed portions 32 of the garment 20 of FIGS. 1–5. Also, the side marginal portions 40 of the garment 80 are wider than in the previous embodiment, so that the elastic members 25 are spaced a greater distance in the transverse direction from the absorbent assembly 23.

Figure 9:
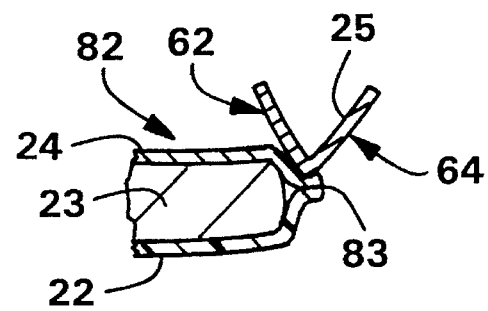
FIG. 9 is a section view similar to FIG. 5, but illustrating components of a further alternative disposable absorbent article according to the present invention.

In contrast to the embodiment of FIG. 8, an alternative incontinence garment 82 shown in FIG. 9 includes an outer cover 22 and bodyside liner 24 that together define a recessed portion 83. Desirably, both the outer cover 22 and the bodyside liner 24 are generally I-shaped so that their side edges together define the recessed portions 83 approximately midway between the end edges 30. The elastic members 25 are bonded to the bodyside liner 24 to span the recessed portion 83, and at least a portion of the outer zone 64 of each of the elastic members 25 extends transversely outward from the side edges of the outer cover 22 and bodyside liner. The recessed portions 83 desirably constitute from about 15 to about 75 percent of the longitudinal length dimension of the garment 82, but could alternatively extend the full length.

Figure 10:
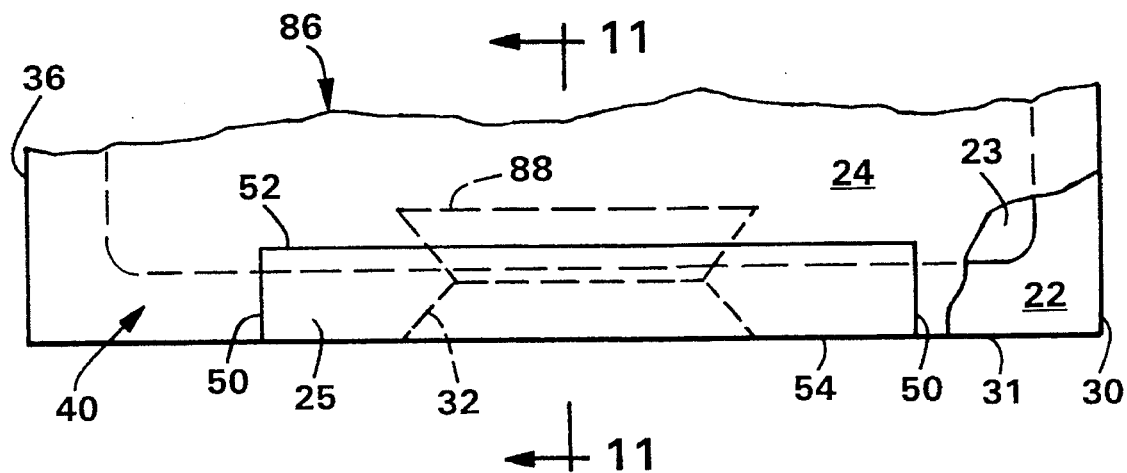
FIG. 10 is a top plan view of portions of several components of a still further alternative disposable absorbent article according to the present invention, in a flat and stretched condition and with portions broken away for purposes of illustration.
Figure 11:
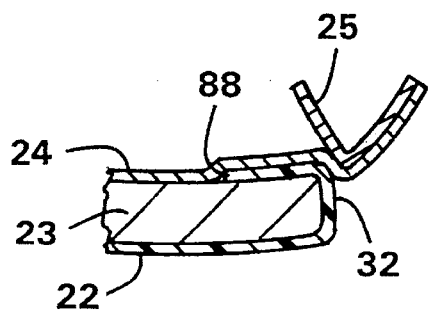
FIG. 11 is an enlarged section view of the absorbent article of FIG. 10 taken generally from the plane of the line 11—11 in FIG. 10, although not in a flat and stretched condition.

With reference to FIGS. 10 and 11, a further alternative incontinence garment 86 according to the present invention includes an outer cover 22 with side edges 31 shaped to define guard portions 88, only one of which is shown. The guard portions 88 may be formed by slitting the outer cover 22 at spaced locations so that the portion resulting between the slits, the guard portion, can be folded over the side edges of the absorbent assembly 23. The guard portions 88 are then positioned on the absorbent assembly 23 beneath the bodyside liner 24 and may be adhesively bonded to the absorbent assembly 23. The guard portions 88 can also be formed by folding the entire side marginal portions 40 over the absorbent assembly 23.

Desirably, the guard portion 88 has a length dimension measured parallel to the longitudinal axis of the garment 86 of from about 10 to about 40 centimeters, and more particularly from about 15 to about 35 centimeters. The guard portion 88 also has a width dimension defined by the transverse extent of the slits of from about 10 to about 50 millimeters, and more desirably from about 20 to about 40 millimeters.

The garment 86 is assembled by forming the guard portions 88 in the outer cover 22 and folding the guard portions over the side edges of the absorbent assembly 23. The folded over guard portions 88 define recessed portions 32 of the side edges 31 of the outer cover 22. The bodyside liner 24 is then bonded to the guard portions 88 and side edges 31 of the outer cover 22. The elastic members 25 are then bonded to the bodyside liner 24 so that they span the recessed portions 32. In this way, the guard portions 88 serve to minimize side leakage while the recessed portions 32 enhance comfort and establish a path of air permeability.

The foregoing detailed description has been for the purpose of illustration. Thus, a number of modifications and changes may be made without departing from the spirit and scope of the present invention. For instance, alternative or optional features described as part of one embodiment can be used to yield another embodiment. Therefore, the invention should not be limited by the specific embodiments described, but only by the claims.

We claim:

1. An absorbent article, comprising:

an outer cover having longitudinal end edges and longitudinal side edges extending between the end edges, each side edge being shaped to define a recessed portion approximately midway between the longitudinal end edges;

a bodyside liner bonded to the outer cover;

an absorbent assembly disposed between the bodyside liner and outer cover, at least one of the bodyside liner and outer cover forming side marginal portions which extend beyond the absorbent assembly; and elastic members comprising an air-permeable material and having opposite end edges, opposite inner and outer edges extending between the end edges and defining a width dimension, an inner zone adjacent the inner edge, and an outer zone adjacent the outer edge;

wherein the outer zone of each of the elastic members is bonded to one of the side marginal portions such that the elastic members span the recessed portions and at least a portion of the outer zone of each elastic member is positioned transversely outward from the side edge of the outer cover, the inner zone of each of the elastic members forms a freestanding cuff, the elastic members are elasticized over substantially the entire width dimension, and the absorbent article has a leg cuff tension of at least about 0.2 kilogram.

2. The absorbent article of claim 1, wherein the absorbent article has a leg cuff tension of at least about 0.25 kilogram.

3. The absorbent article of claim 1, wherein the elastic members comprise a liquid-impermeable material.

4. The absorbent article of claim 1, wherein the inner zone has a width dimension between the inner edge and the outer zone of at least about 4 millimeters and the outer zone has a width dimension between the outer edge and the inner zone of at least about 6 millimeters.

5. The absorbent article of claim 1, wherein the elastic members have a width dimension between the inner and outer edges of from about 15 to about 70 millimeters.

6. The absorbent article of claim 5, wherein at least a portion of the outer zone of each of the elastic members extends transversely outward from the side edges of the bodyside liner.

7. The absorbent article of claim 1, wherein the elastic members have a three panel tension value of at least about 100 grams.

8. The absorbent article of claim 1, wherein the elastic members have an eight panel tension value of at least about 15 grams.

9. The absorbent article of claim 1, wherein the side edges of the outer cover are shaped to define a guard portion and the guard portion is folded onto the absorbent assembly to define the recessed portion.

10. An absorbent article, comprising:

an outer cover having longitudinal end edges and longitudinal side edges extending between the end edges, each side edge being shaped to define a recessed portion approximately midway between the longitudinal end edges;

a bodyside liner bonded to the outer cover;

an absorbent assembly disposed between the bodyside liner and outer cover, at least one of the bodyside liner and outer cover forming side marginal portions which extend beyond the absorbent assembly; and elastic members having opposite end edges, opposite inner and outer edges extending between the end edges and defining a width dimension, an inner zone adjacent the inner edge, and an outer zone adjacent the outer edge, the elastic members being elasticized over substantially the entire width dimension and comprising a breathable material having an air porosity value of at least about 150 cubic feet per minute per square foot in a relaxed state;

wherein the outer zone of each of the elastic members is bonded to one of the side marginal portions such that the elastic members span the recessed portions and at least a portion of the outer zone of each elastic member is positioned transversely outward from the side edge of the outer cover, and the inner zone of each of the elastic members forms a freestanding cuff.

11. The absorbent article of claim 10, wherein the absorbent article has a leg cuff tension of at least about 0.2 kilogram.

12. An absorbent article, comprising:

an outer cover having longitudinal end edges and longitudinal side edges extending between the end edges, each side edge being shaped to define a recessed portion approximately midway between the longitudinal end edges;

a bodyside liner bonded to the outer cover;

an absorbent assembly disposed between the bodyside liner and outer cover, at least one of the bodyside liner and outer cover forming side marginal portions which extend beyond the absorbent assembly; and elastic members having a length dimension extending between opposite end edges of from about 20 to about 50 centimeters, a width dimension extending between opposite inner and outer edges of from about 15 to about 70 millimeters, an inner zone adjacent the inner edge, and an outer zone adjacent the outer edge and abutting the inner zone, the elastic members comprising an elastomeric nonwoven fibrous web material composed of at least one layer of nonwoven fabric secured to an elastic layer, the elastic members having a three panel tension value of at least about 100 grams and an air porosity value of at least about 150 cubic feet per minute per square foot in a relaxed state;

wherein the outer zone of each of the elastic members is bonded to one of the side marginal portions such that the elastic members span the recessed portions and at least a portion of the outer zone of each elastic member is positioned transversely outward from the side edge of the outer cover, the inner zone of each of the elastic members forms a freestanding cuff, and the absorbent article has a leg cuff tension of at least about 0.2 kilogram.

13. The absorbent article of claim 12, wherein the absorbent article has a leg cuff tension of at least about 0.25 kilogram.

14. The absorbent article of claim 12, wherein the elastic members have an eight panel tension value of at least about 25 grams.

15. The absorbent article of claim 12, wherein at least a portion of the outer zone of each of the elastic members extends transversely outward from side edges of the bodyside liner.

16. The absorbent article of claim 12, wherein the elastic members comprise a liquid-impermeable material.

* * * * *